United States Patent [19]

Yamamoto

[11] Patent Number: 4,666,578
[45] Date of Patent: May 19, 1987

[54] METHOD OF MEASURING TOTAL PROTEIN OF SAMPLE WITH THE AID OF ELECTROPHORETIC IMAGE

[75] Inventor: Hidehiko Yamamoto, Hachioji, Japan

[73] Assignee: Olympus Optical Co., Ltd., Tokyo, Japan

[21] Appl. No.: 832,221

[22] Filed: Feb. 24, 1986

[30] Foreign Application Priority Data

Feb. 27, 1985 [JP] Japan .................................. 60-36606

[51] Int. Cl.$^4$ ..................... C25D 13/06; C25D 13/16; C25B 7/00
[52] U.S. Cl. ............................... 204/183.3; 204/180.1; 204/299 R; 204/300 R
[58] Field of Search ............. 204/183.3, 180.1, 299 R, 204/300 R

[56] References Cited

U.S. PATENT DOCUMENTS

| | | | |
|---|---|---|---|
| 3,869,365 | 3/1975 | Sunden | 204/183.3 |
| 3,912,609 | 10/1975 | Arlinger | 204/183.1 |
| 3,941,678 | 3/1976 | Akiyama | 204/183.3 |
| 4,154,669 | 5/1979 | Goetz | 204/180.1 |
| 4,181,594 | 1/1980 | Rizk et al. | 204/299 R |
| 4,315,812 | 2/1982 | Karlson | 204/183.3 |
| 4,416,762 | 11/1983 | Akiyama | 204/183.3 |
| 4,456,513 | 6/1984 | Kawai et al. | 204/183.3 |
| 4,569,739 | 11/1986 | Klinkowski | 204/180.1 |
| 4,594,064 | 6/1986 | Anderson | 204/299 R |

FOREIGN PATENT DOCUMENTS 3127007 3/1982 Fed. Rep. of Germany ... 204/180 R

Primary Examiner—Arthur P. Demers
Attorney, Agent, or Firm—Parkhurst & Oliff

[57] ABSTRACT

A method of measuring an amount of total protein $TP_i$ of a test sample from an electrophoretic image of the test sample including a step of forming an electrophoretic image of a standard sample having a known amount of total protein $TP_1$, a step of integrating absorbance values of the electrophoretic image of the standard sample to derive an integrated value of concentration $D_1$ of the electrophoretic image, a step of integrating absorption values of the electrophoretic image of the test sample to derive an integration value of concentration $D_i$ of the electrophoretic image of the test sample, and a step of deriving the amount of total protein $TP_i$ of the test sample in accordance with an equation of $$TP_i = \frac{D_i}{D_1} \cdot TP_1.$$

14 Claims, 7 Drawing Figures

Substrate

Densitometer

METHOD OF MEASURING TOTAL PROTEIN OF SAMPLE WITH THE AID OF ELECTROPHORETIC IMAGE

BACKGROUND OF THE INVENTION

Field of the Invention and Related Art Statement

The present invention relates to a method of measuring an amount of total protein contained in a serum sample with the aid of an electrophoretic image formed by an electrophoretic apparatus.

In known electrophoretic apparatuses, a fraction image pattern representing fraction images of albumin (Alb), $\alpha_1$-globulin ($\alpha_1$-G), $\alpha_2$-globulin ($\alpha_2$-G), $\beta$-globulin ($\beta$-G) and $\gamma$-globulin ($\gamma$-G), fraction percentages of these protein components and A/G value (a ratio of albumin relative to globulin) are generally recorded on a test report. Nowadays, it has become important to monitor a variation in absolute amounts of respective protein components in addition to a variation in fraction percentages which represent relative amounts of respective protein components. Therefore, it has been practised to measure an amount of total protein of a sample by means of a separate biochemical analyzer and the measured amount of total protein is entered into the electrophoretic apparatus and absolute amounts of respective substances of the sample are calculated by multiplying the fraction percentages by the amount of total protein. The absolute amounts thus calculated are also printed on the test report.

However, the operation of measuring the amounts of total protein of respective samples by the separate biochemical analyzer and entering the amounts of total protein thus measured into the electrophoretic apparatus is very cumbersome and there might be produced any error in the identification of samples. Moreover, the number of test items which can be analyzed by the biochemical analyzer is decreased by one.

SUMMARY OF THE INVENTION

The present invention has for its object to provide a novel and useful method of measuring an amount of total protein with the aid of the electrophoretic apparatus.

According to the invention, a method of measuring an amount of total protein contained in a sample comprises the steps of forming electrophoretic images of a standard sample having a known amount of total protein and of a test sample having an unknown amount of total protein;

deriving an integrated value of concentration of the electrophoretic image of the standard sample;

deriving an integrated amount of concentration of the electrophoretic image of the test sample; and calculating the unknown amount of protein of the test sample in accordance with the known amount of total protein of the standard sample and the integrated values of concentration of the electrophoretic images of the standard sample and test sample.

In a preferred embodiment of the method according to the invention, the integrated value of concentration of electrophoretic image is derived by optically scanning the electrophoretic image in a two dimensional manner to derive an image signal, supplying the image signal to a log-amplifier to derive an absorption value which is in proportion to the concentration of protein in a sample, and integrating the absorption value over the whole electrophoretic image.

DESCRIPTION OF THE PREFERRED EMBODIMENTS

In an embodiment of the electrophoretic apparatus which is preferably used in the method according to the invention, a number of test samples, e.g. thirty test samples are applied on a substrate made of cellulose acetate by means of an applicator having thirty applying tips. Then the substrate is placed in an electrophoretic chamber for a given time period. Next, after the substrate is dyed, decolored and dried, the substrate is fed into a densitometer to measure an absorption of electrophoretic images of test samples successively.

Figure 1:
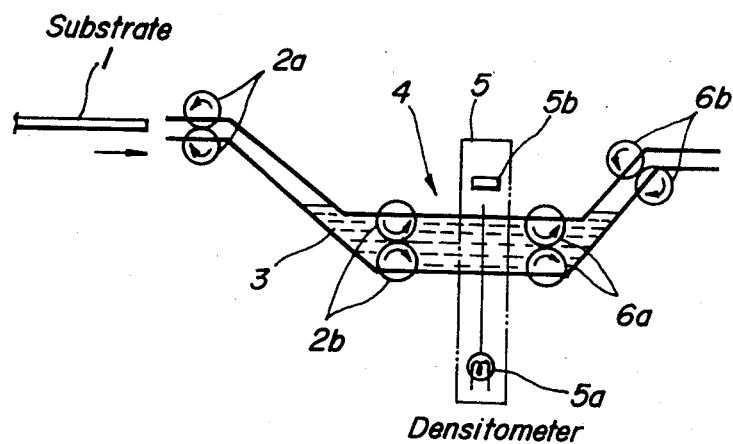
FIG. 1 is a schematic side view showing an embodiment of an electrophoretic apparatus for use in the method according to the invention.
Figure 2:
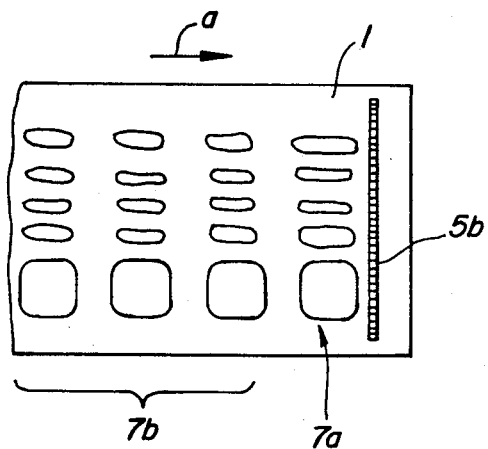
FIG. 2 is a schematic plan view illustrating a positional relation of a linear image sensor array with respect to a substrate shown in FIG. 1.

FIG. 1 is a schematic view showing a principal construction of the densitometer of electrophoretic apparatus for use in the method according to the invention. A substrate 1 which has been previously dyed, decolored and dried is fed by feeding rollers 2a, 2b into a photometering section 4 containing decalin 3 for making the substrate 1 transparent. The substrate 1 is photometered by the photometer device 5 and then is discharged by means of discharge rollers 6a, 6b. The photometer device 5 comprises a light source 5a arranged below the substrate 1 for emitting a light flux and a linear image sensor array 5b arranged above the substrate 1. The linear image sensor array 5b may be formed by linear CCD or photodiode array and is aligned in a direction perpendicular to a feeding direction a of the substrate 1 as illustrated in FIG. 2.

In the present embodiment, it is assumed that thirty samples are simultaneously applied on the substrate 1. Among these samples a first sample viewed in the feeding direction of the substrate is formed by a standard sample having a known amount of total protein, and the remaining twenty nine samples are formed by test samples having unknown amounts of total protein. In FIG. 2, an electrophoretic image of the standard sample is denoted by a reference numeral 7a and then electrophoretic images of test samples are represented by a reference numeral 7b. According to the invention an integrated value of concentration of an electrophoretic image is derived by moving the substrate 1 in a stepwise manner in the direction a.

Figure 3:
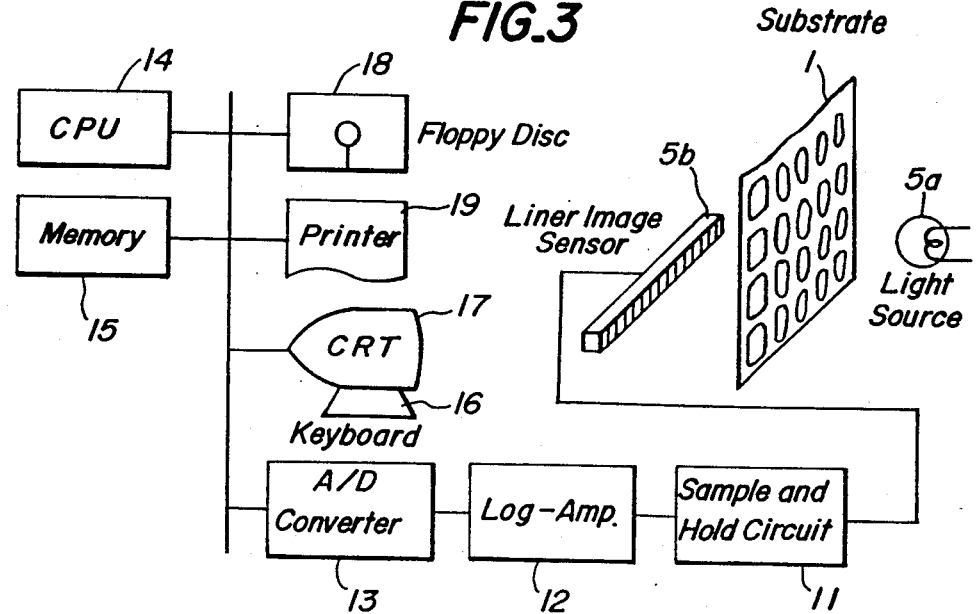
FIG. 3 is a block diagram depicting an embodiment of a data processing circuit.

FIG. 3 is a block diagram illustrating an embodiment of a data processing circuit for carrying out the method according to the invention. In the present embodiment, various kinds of protein components contained in serum samples of human beings are to be analyzed. The substrate 1 bearing electrophoretic images of standard and test serum samples is fed through the densitometer 5 comprising the light source 5a and the linear image sensor array 5b at a constant speed, e.g. 8 mm/sec. An output photoelectrically converted image signal from the linear image sensor array 5b is sampled by a sample and hold circuit 11 in synchronism with the stepwise movement of the substrate 1. The signal thus sampled and held is amplified by a log-amplifier 12 and is converted into a signal representing an optical absorbance of electrophoretic image, which absorbance is, in turn, proportional to a concentration of protein of a sample. Then, the absorption signal is converted into digital samples by an A/D converter 13. The digital samples thus obtained are supplied to a memory 15 and are stored therein under the control of a central processing unit (CPU) 14 after effecting necessary signal processings such as smoothing and auto-zero adjustment for correcting variation of a base line due to fluctuation of light intensity. The apparatus further comprises a keyboard 30 and a cathode ray tube (CRT) 31 for entering and monitoring various commands, data and images.

In the present embodiment, a known amount of total protein (TP$_1$) contained in the standard sample is entered into the memory 15 with the aid of the keyboard 16 and CRT 17.

Figure 4:
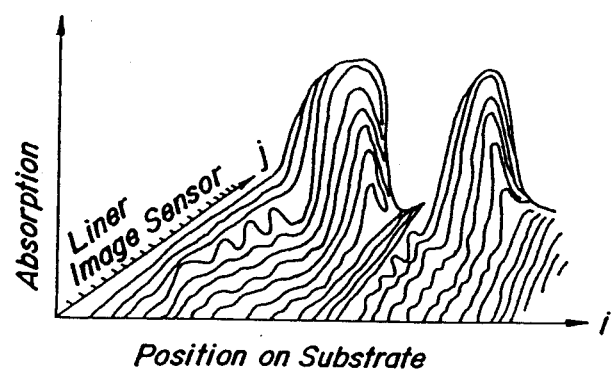
FIGS. 4, 5, 6 and 7 are diagrams for explaining the operation of the data processing circuit illustrated in FIG. 2.
Figure 5:
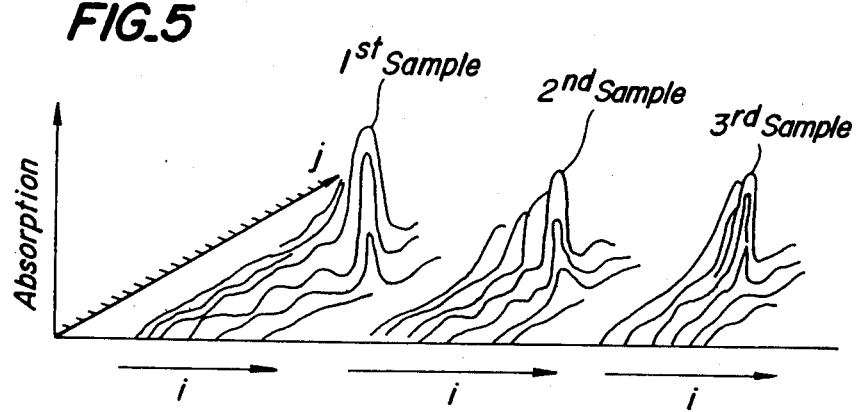

By photometering the electrophoretic image, while the substrate 1 is fed in a stepwise manner, in the memory 15 there is stored three dimensional data of the absorption of electrophoretic image as illustrated in FIG. 4. Then the samples stored in the memory 15 are separated into respective samples as illustrated in FIG. 5 and integrated concentrations D$_1$, D$_2$ . . . D$_N$ of electrophoretic images of the standard sample and test samples are calculated. In general, the integrated value D of concentration can be represented by $$D = \sum_i \sum_j D_{ij} \quad (1)$$

wherein D$_{ij}$ is data obtained in i$^{th}$ pitch movement from a j$^{th}$ light receiving element of the linear image sensor array 5b. In general, the absorption value obtained by optically scanning the electrophoretic image formed on the substrate is in proportion to a concentration of protein. Therefore, the integrated value D of the whole electrophoretic image of a sample is proportional to a concentration of total protein contained in the sample. Now a known amount of total protein of the standard sample and an unknown amount of total protein of a test sample are denoted as TP$_1$ and TP$_i$, respectively and the integrated values of concentration of the electrophoretic images of the standard and test samples are represented as D$_1$ and D$_i$, respectively. Then the following equation (2) can be derived.

$$\frac{TP_i}{TP_1} = \frac{D_i}{D_1} \quad (2)$$

$$TP_i = \frac{D_i}{D_1} \cdot TP_1$$

This means that the unknown amount of total protein TP$_i$ can be calculated in accordance with the above equation (2) when the integrated values of concentration D$_1$ and D$_i$ of the electrophoretic images of the standard sample and test sample are detected and the known amount of total protein TP$_1$ is given.

Figure 6:
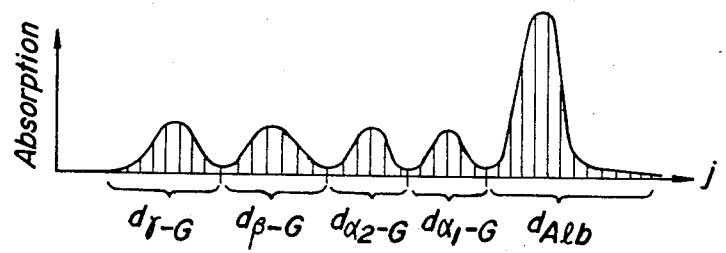

As is well known in the art an electrophoretic image of a sample is composed of fraction images of different protein components, e.g. albumin, $\alpha_1$-globulin, $\alpha_2$-globulin, $\beta$-globulin and $\gamma$-globulin. It has been found that these substances are dyed by a dyeing liquid to different degrees. For instance, Ponceau-3R is used as the dyeing liquid, the concentration of the fraction image of albumin is higher than that of $\gamma$-globulin. In the present embodiment, in order to compensate the difference in dyeing degree of respective protein components, there are introduced dye correction coefficients $k_{Alb}$, $k_{\alpha 1-G}$, $k_{\alpha 2-G}$, $k_{\beta-G}$ and $k_{\gamma-G}$ which may be determined in accordance with the dye and a photometering wavelength to be used. These coefficients are previously entered into the memory 15 with the aid of the keyboard 16. Further, the electrophoretic image is divided into fraction images and integrated values of concentration of respective fraction images $d_{Alb}$, $d_{\alpha 1-G}$, $d_{\alpha 2-G}$, $d_{\beta-G}$ and $d_{\gamma-G}$ are derived as illustrated in FIG. 6. Then a corrected integration value of concentration D' of electrophoretic image is calculated in accordance with the following equation by using the correction coefficients.

$$D' = k_{Alb} \cdot d_{Alb} + k_{\alpha 1-G} \cdot d_{\alpha 1-G} + k_{\alpha 2-G} \cdot d_{\alpha 2-G} + k_{\beta-G} \cdot d_{\beta-G} + k_{\gamma-G} \cdot d_{\gamma-G} \quad (3)$$

Then an amount of total protein of a test sample TP$_i$ is derived by the following equation.

$$TP_i = \frac{D_i'}{D_1'} \cdot TP_1 \quad (4)$$

The following Table 1 shows an example of the dye correction coefficients.

TABLE 1

| $k_{Alb}$ | $k_{\alpha 1-G}$ | $k_{\alpha 2-G}$ | $k_{\beta-G}$ | $k_{\gamma-G}$ |
| --- | --- | --- | --- | --- |
| 0.430 | 0.428 | 0.426 | 0.423 | 0.420 |

The electrophoretic image may be divided into respective fraction images in accordance with various processes. In one embodiment of the dividing method, the following steps are performed to derive integration values of concentration for respective fraction images.

(a) a center scanning line is selected from all the scanning lines;

(b) fraction points are detected on the center scanning line;

(c) fraction lines passing through the fraction points are drawn in the direction perpendicular to the scanning line; and (d) concentration values within regions divided by the fraction lines are integrated to derive the integrating values of concentration of respective protein components In another method of dividing the electrophoretic image, the following steps are carried out.

Figure 7:
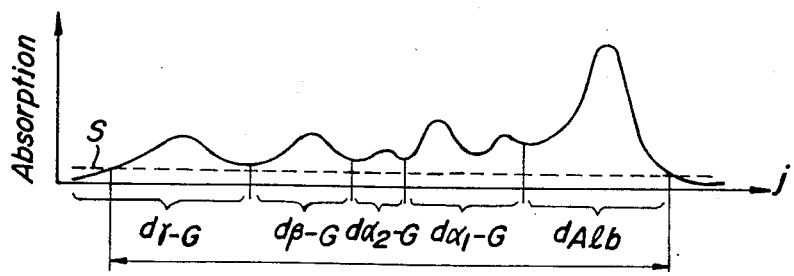

(a) an electrophoretic expansion length L is detected for each scanning lines by comparing absorption values with a threshold level S as illustrated in FIG. 7;

(b) the electrophoretic expansion length L is divided into fraction lengths in proportion to standard fraction image lengths;

(c) concentration values within respective fraction lengths are integrated to derive integration values of fraction regions along respective scanning lines; and (d) the integration values of respective protein components for respective scanning lines are accumulated to derive the integration values of respective fraction images.

When samples are applied onto the substrate by means of the applicator having a number of applying tips, amounts of samples applied on the substrate are slightly varied from each other. Further the degree of dyeing is varied in accordance with the positions of samples in the dyeing vessel. In the present embodiment, in order to remove the above mentioned variations, there are introduced second correction coefficients $K_1, K_2 \ldots K_N$ for compensating the variation in amount of applied samples on the substrate. The second correction coefficients may be derived in the following manner. At first, the standard sample having the known amount of total protein is applied on the substrate by means of all the thirty applying tips of the applicator and the substrate is subjected to the electrophoresis to form thirty electrophoretic images of the same standard sample. Then these electrophoretic images are photoelectrically scanned to derive integration values of concentration of the electrophoretic images $d_1, d_2 \ldots d_N$. The above operation is effected once or more than once. In the latter case, a plurality of integration values of concentration for respective electrophoretic images are averaged to derive an averaged integration value of concentration for respective applying tips. Then the integration values of concentration $d_1, d_2 \ldots d_N$ thus obtained for all the electrophoretic images are averaged to derive a reference integration value of concentration $d_R$. Then correction coefficients $K_1, K_2 \ldots K_N$ are calculated by dividing the reference integration value of concentration $d_R$ by respective integration values of concentration $d_1, d_2 \ldots d_N$.

$$\left.\begin{array}{l} K_1 = \dfrac{d_R}{d_1} \\ K_2 = \dfrac{d_R}{d_2} \\ \vdots \\ K_N = \dfrac{d_R}{d_N} \end{array}\right\} \quad (5)$$

The following Table 2 represents an example of actual values of the correction coefficients $K_1, K_2 \ldots K_N$ derived in the manner explained above.

TABLE 2

| $K_1$ | $K_2$ | $K_3$ | $K_{30}$ |
|---|---|---|---|
| 1.02 | 1.05 | 0.98 | 0.87 |

It should be noted that when a correction coefficient $K_i$ for an applying tip of the applicator is larger than 1.00, an amount of a sample applied by the relevant applying tip is larger than an average amount. Therefore, an integration value of concentration $D_i$ can be compensated for by dividing $D_i$ by $K_i$.

The correction coefficients $K_1, K_2 \ldots K_N$ may be stored in the memory 15 with the aid of the keyboard 16 and CRT 17 or may be calculated and stored in the memory 15 in an automatic manner by means of the CPU 14. In the latter case, it is sufficient for the operator to enter into the CPU 14 a command requesting the operation of calculating and storing the correction coefficients.

After the correction coefficients $K_1, K_2 \ldots K_N$ have been stored in the memory 15 in the manner explained above, test samples having unknown amounts of total proteins are applied on the substrate together with the standard sample having the known amount of total protein, and then the substrate is subjected to the electrophoresis to form electrophoretic images on the substrate. Next, the electrophoretic image of the test samples and standard sample are optically scanned and integration values of concentration of respective electrophoretic images $D_1, D_2 \ldots D_N$ are calculated. Then, an amount of total protein of a test sample $TP_i$ is calculated in accordance with the following equation.

$$TP_i = \frac{D_i \cdot K_1}{D_1 \cdot K_i} \cdot TP \quad (6)$$

The amounts of total protein of the test samples thus calculated are stored in the floppy disc 18.

In the present embodiment, among all the absorption values of the test samples stored in the memory 15 are extracted absorption values on scanning lines passing through canter lines of respective electrophoretic images of the test samples. Then, fraction percentages and ratios A/G are calculated from the extracted absorption values and are stored in the floppy disc 18. At the same time, amounts of respective protein components are calculated by multiplying the fraction percentages by the amount of total protein calculated according to the equation (6), and are stored in the floppy disc 18. Further, the extracted absorption values are normalized by the auto-span treatment. The above operation is performed for successive electrophoretic images of the test samples formed on the substrate, and amounts of total protein, fraction percentages, A/G ratios, amounts of respective protein components and normalized absorption values for all the twenty nine test samples are stored in the floppy disc 18. Then the amount of total protein, fraction percentages, A/G ratio, amounts of respective protein components and electrophoretic image pattern are recorded on a test report by means of the printer 19 under the control of the CPU 14.

As explained above, in the present embodiment, the standard sample having a known amount of total protein is applied on the substrate together with the test samples and unknown amounts of total protein of the test samples are derived from the known amount of total protein of the standard sample, the integration value of concentration of the electrophoretic image of the standard sample, the integration values of concentration of the electrophoretic images of the test samples and the first and second correction coefficients for correcting difference in dyeing condition and variations in amounts of samples applied on the substrate. Therefore, the amounts of total protein of the test samples can be always quantitized precisely.

The present invention is not limited to the embodiments explained above, but many modifications and alternations may be conceived by those skilled in the art within the scope of the invention.

For instance, in the above embodiment the densitometer comprises the linear image sensor array, but a single light receiving element may be moved in the main scanning direction together with the light source in synchronism with the stepwise movement of the substrate to effect the raster scanning. Further, use may be made of a two-dimensional image sensor and an objective lens for forming an image of an electrophoretic image of a sample on the image sensor. In such a case, the pitch of the stepwise movement of the substrate may be longer and thus the control for the movement may be simpler.

Further, a condition of an electrophoretic image due to various factors, e.g. unevenness in sample application may be judged on the basis of the absorption values, and when the condition of electrophoretic image is judged to be bad, the calculation of amount of total protein may be dispensed with. The condition of electrophoretic image may be judged by various methods. For instance, maximum values, average values or integrated values of absorption values in each scanning lines are derived and a pattern is drawn by the values thus derived. Then a length of a pattern viewed in the feeding direction of the substrate is detected and is compared with a standard length or the number of inflection points of the pattern is detected and is compared with a standard value.

When a calculated amount of total protein is extraordinarily high or low, the amount may not be printed out or may be printed with an abnormal mark.

Further, in the above embodiment, an integration value of concentration is derived by integrating absorption values of whole the electrophoretic image. However, it is also possible to calculated an integration value of concentration by integrating absorption values of a single scanning line passing through the center of the electrophoretic image.

Moreover, in the above embodiment, a standard sample having a known amount of total protein and test samples having unknown amounts of total protein are applied on one and the same substrate and the unknown amounts of total protein of the test samples are calculated from the known amount of total protein of the standard sample, the integration value of concentration of electrophoretic image of the standard sample and the integration values of concentration of electrophoretic images of the test samples. However, the standard sample is not always necessary to be applied on the substrate. In such a case, a number of aliquots of a plurality of standard samples having different known amounts of total protein are applied on a plurality of substrates, and a calibration curve or a conversion coefficient representing a relation between an amount of total protein and an integration value of concentration of electrophoretic image is derived. Then, only test samples are applied on a substrate and amounts of total protein of the test samples may be derived from the calibration curve or conversion coefficient. In this case, it is preferable to derive calibration curves or conversion coefficients for respective applying tips of the sample applicator.

As explained above in detail, according to the invention, an amount of total protein of a sample can be derived from an electrophoretic image formed by the electrophoretic apparatus. Therefore, it is possible to dispense the cumbersome operation of analyzing amounts of total protein of test samples by means of the biochemical analyzer and of entering the analyzed amounts of total protein into the electrophoretic apparatus. Therefore, the biochemical analyzer can be utilized much more efficiently.

What is claimed is:

1. a method of measuring an amount of total protein contained in a sample comprising the steps of
    forming electrophoretic images of a standard sample having a known amount of total protein and of a test sample having an unknown amount of total protein;
    deriving an integrated value of concentration of the electrophoretic image of the standard sample;
    deriving an integrated amount of concentration of the electrophoretic image of the test sample; and
    calculating the unknown amount of protein of the test sample in accordance with the known amount of total protein of the standard sample and the integrated values of concentration of the electrophoretic images of the standard sample and test sample.

2. A method according to claim 1, wherein said electrophoretic images of the standard and test samples are formed by applying the standard and test samples on a single substrate and by subjecting the substrate to electrophoresis.

3. A method according to claim 1, wherein an integrated value of concentration of an electrophoretic image of a sample is derived by scanning the electrophoretic image photoelectrically to derive a first electric signal representing a transmittivity of the electrophoretic image, supplying the first electric signal ot a log-amplifier to derive a second electric signal representing an absorption of the electrophoretic image and integrating the second electric signal to derive the integrated value of concentration of the electrophoretic image.

4. A method according to claim 3, wherein said electrophoretic image is scanned two-dimensionally and said second electric signal is integrated over whole the electrophoretic image.

5. A method according to claim 3, wherein said electrophoretic image is scanned linearly along a center line of the electrophoretic image and said second electric signal is integrated along the center line of the electrophoretic image.

6. A method according to claim 1, further comprising a step of correcting an integrated value of concentration of electrophoretic image of a sample.

7. A method according to claim 6, wherein said correcting step comprises deriving correction coefficients $k_{Alb}$, $k_{\alpha 1\text{-}G}$, $k_{\alpha 2\text{-}G}$, $k_{\beta\text{-}G}$ and $k_{\gamma\text{-}G}$ for correcting difference in dyeing degree for respective protein components, deriving integrated values of concentration $d_{Alb}$, $d_{\alpha 1\text{-}G}$, $d_{\alpha 2\text{-}G}$, $d_{\beta\text{-}G}$ and $d_{\gamma\text{-}G}$ for fraction images of respective protein components, and deriving an integrated value of concentration D of the electrophoretic image as a sum of products of the integrated values of concentration of fraction images and corresponding correction coefficients:

$$D = k_{Alb} \cdot d_{Alb} + k_{\alpha 1\text{-}G} \cdot d_{\alpha 1\text{-}G} + k_{\alpha 2\text{-}G} \cdot d_{\alpha 2\text{-}G} + k_{\beta\text{-}G} \cdot d_{\beta\text{-}G} + k_{\gamma\text{-}G} \cdot d_{\gamma\text{-}G}.$$

8. A method according to claim 7, wherein said correction coefficients are determined in accordance with a wavelength of light by means of which the electrophoretic image is optically scanned.

9. A method according to claim 2, wherein an electrophoretic image of the standard sample and a plurality of electrophoretic images of a plurality of test samples are formed on the same substrate and the method further comprises a step of correcting variation in amounts of samples applied on the substrate.

10. A method according to claim 9, wherein said correcting step comprises
    forming a plurality of electrophoretic images of the standard sample on a substrate, deriving integrated values of concentration $d_1, d_2 \ldots d_N$ of said plurality of electrophoretic images of the standard sample;

deriving an average value $d_R$ of said integrated values of concentration $d_1, d_2 \ldots d_N$;

deriving correction coefficients $K_1, K_2 \ldots K_N$ in accordance with said integrated values of concentration and the average value; and deriving corrected integration values of concentration by dividing integrated values $D_1, D_2 \ldots D_N$ of electrophoretic images of test samples by said correction coefficients $K_1, K_2 \ldots K_N$, respectively.

11. A method according to claim 10, wherein said steps of forming the electrophoretic images of the standard sample and deriving the integrated values of concentration of electrophoretic images of the standard sample are performed plural times by using a plurality of substrates, and said average value of integration value is calculated from average values of a plurality of integrated values of concentration.

12. A method according to claim 3, wherein said electrophoretic images of samples are moved in a stepwise manner in a direction perpendicular to an electrophoretic direction and are scanned by means of a linear image sensor array aligned in the electrophoretic direction.

13. A method according to claim 1, further comprising a step of calculating amounts of respective protein components of a sample by multiplying fraction percentages of respective protein components by an amount of total protein of the relevant sample.

14. A method according to claim 1, further comprising a step of detecting condition of electrophoretic images of samples, and deleting a deriving operation of an amount of total protein of a sample when the condition of electrophoretic image of the relevant sample is detected to be abnormal.

* * * * *